United States Patent

Roger

[11] Patent Number: 6,056,752
[45] Date of Patent: May 2, 2000

[54] FIXATION OF CRUCIATE LIGAMENT GRAFTS

[75] Inventor: Gregory J. Roger, Crows Nest, Australia

[73] Assignee: Smith & Nephew, Inc., Memphis, Tenn.

[21] Appl. No.: 09/177,855

[22] Filed: Oct. 23, 1998

[30] Foreign Application Priority Data

Oct. 24, 1997 [AU] Australia ................................. PP0007

[51] Int. Cl.$^7$ .................................................. A61B 17/56
[52] U.S. Cl. ............................... 606/72; 606/151; 623/13
[58] Field of Search ............................... 606/72, 88, 151, 606/232; 623/13

[56] References Cited

U.S. PATENT DOCUMENTS

| | | | |
|---|---|---|---|
| 64,499 | 6/1867 | Miller | 606/232 X |
| 2,242,003 | 5/1941 | Lorenzo . | |
| 2,267,925 | 12/1941 | Johnston . | |
| 3,683,422 | 8/1972 | Stemmer et al. | 623/18 X |
| 3,896,500 | 7/1975 | Rambert et al. | 623/18 X |
| 4,085,466 | 4/1978 | Goodfellow et al. . | |
| 4,210,148 | 7/1980 | Stivala | 128/335 |
| 4,400,833 | 8/1983 | Kurland | 623/18 X |
| 4,409,974 | 10/1983 | Freeland | 128/335 |
| 4,463,753 | 8/1984 | Gustilo . | |
| 4,537,185 | 8/1985 | Stednitz . | |
| 4,584,722 | 4/1986 | Levy et al. | 623/13 |
| 4,708,132 | 11/1987 | Silvestrini | 128/92 |
| 4,728,332 | 3/1988 | Albrektsson . | |
| 4,744,793 | 5/1988 | Parr et al. . | |
| 4,772,286 | 9/1988 | Goble et al. . | |
| 4,773,910 | 9/1988 | Chen et al. | 623/13 |
| 4,775,380 | 10/1988 | Seedhom et al. . | |
| 4,823,794 | 4/1989 | Pierce | 128/335 |
| 4,828,562 | 5/1989 | Kenna . | |
| 4,870,957 | 10/1989 | Goble et al. . | |
| 4,896,668 | 1/1990 | Popoff et al. | 606/74 |
| 4,927,421 | 5/1990 | Goble et al. . | |
| 4,950,270 | 8/1990 | Bowman et al. . | |
| 4,979,956 | 12/1990 | Silvestrini | 623/13 |
| 4,988,351 | 1/1991 | Paulos et al. . | |

(List continued on next page.)

FOREIGN PATENT DOCUMENTS

| | | |
|---|---|---|
| 14615/28 | 7/1928 | Australia . |
| 59999/90 | 2/1991 | Australia . |
| 0172130 | 2/1986 | European Pat. Off. . |

(List continued on next page.)

OTHER PUBLICATIONS

European Patent Abstracts, Week 9240, p. 235, EP 506420–A1.
European Patent Abstracts, Week 9240, p. 189, EP 506213–A1.
European Patent Abstracts, Week 9237, p. 161, EP 502698–A1.
European Patent Abstracts, Week 9212, p. 267, EP 475–889–A.
European Patent Abstracts, Week 9208, p. 99, EP 471–419–A.
European Patent Abstracts, Week 9206, p. 99, EP 469–441–A.
European Patent Abstracts, Week 9144, p. 250, EP 454–601–A.
European Patent Abstracts, Week 9143, p. 28, EP 452–442–A.
European Patent Abstracts, Week 9106, p. 29, EP 411–109–A.

(List continued on next page.)

*Primary Examiner*—Michael Buiz
*Assistant Examiner*—Julian W. Woo
*Attorney, Agent, or Firm*—Fish & Richardson P.C.

[57] ABSTRACT

The present invention comprises a method for the reconstruction of a cruciate ligament of a patient. A connection device for connecting a cruciate ligament replacement graft to the femur of a patient is also described. The arrangement can result preferably in the femoral end of the graft being held in the femoral hole without any spring or elasticity in the connection between the graft and the femoral bone. At this end of the graft, at least, the practical and theoretical problems of screw fixation are avoided.

29 Claims, 5 Drawing Sheets

U.S. PATENT DOCUMENTS

| | | |
|---|---|---|
| 4,997,433 | 3/1991 | Goble et al. .............................. 606/64 |
| 5,037,422 | 8/1991 | Hayhurst et al. ......................... 606/72 |
| 5,046,513 | 9/1991 | Gatturna et al. ........................ 128/898 |
| 5,062,843 | 11/1991 | Mahony .................................... 606/73 |
| 5,084,050 | 1/1992 | Draenert . |
| 5,116,337 | 5/1992 | Johnson . |
| 5,116,373 | 5/1992 | Jakob et al. .............................. 623/13 |
| 5,116,375 | 5/1992 | Hofmann . |
| 5,129,902 | 7/1992 | Goble et al. . |
| 5,129,906 | 7/1992 | Ross et al. . |
| 5,139,520 | 8/1992 | Rosenberg . |
| 5,147,362 | 9/1992 | Goble ....................................... 606/72 |
| 5,152,790 | 10/1992 | Rosenberg et al. ....................... 623/13 |
| 5,203,787 | 4/1993 | Noblitt et al. .......................... 606/232 |
| 5,209,753 | 5/1993 | Biedermann et al. . |
| 5,211,647 | 5/1993 | Schmieding . |
| 5,236,461 | 8/1993 | Forte . |
| 5,246,441 | 9/1993 | Ross . |
| 5,281,422 | 1/1994 | Badylak et al. . |
| 5,282,809 | 2/1994 | Kammerer et al. ..................... 606/148 |
| 5,285,040 | 2/1994 | Bruchman et al. . |
| 5,290,217 | 3/1994 | Campos .................................... 600/37 |
| 5,306,301 | 4/1994 | Graf et al. ................................ 623/13 |
| 5,362,294 | 11/1994 | Seitzinger ................................. 600/37 |
| 5,372,604 | 12/1994 | Trott ...................................... 606/232 |
| 5,383,878 | 1/1995 | Roger et al. . |
| 5,443,468 | 8/1995 | Johnson . |
| 5,454,811 | 10/1995 | Huebner . |
| 5,456,685 | 10/1995 | Huebner . |
| 5,470,334 | 11/1995 | Ross et al. . |
| 5,628,766 | 5/1997 | Johnson . |
| 5,632,748 | 5/1997 | Beck et al. . |
| 5,645,588 | 7/1997 | Graf et al. ................................ 623/13 |
| 5,674,224 | 10/1997 | Howell et al. . |
| 5,766,250 | 6/1998 | Chervitz et al. .......................... 623/13 |
| 5,769,894 | 6/1998 | Ferragamo ................................ 623/13 |
| 5,931,869 | 8/1999 | Boucher et al. .......................... 623/13 |

FOREIGN PATENT DOCUMENTS

| | | |
|---|---|---|
| 0241792 | 10/1987 | European Pat. Off. . |
| 0260970 | 3/1988 | European Pat. Off. . |
| 0282789 | 9/1988 | European Pat. Off. . |
| 0317406 | 5/1989 | European Pat. Off. . |
| 0 346 183 | 12/1989 | European Pat. Off. . |
| 0 349 173 | 1/1990 | European Pat. Off. . |
| 0374088 | 6/1990 | European Pat. Off. . |
| 451932A1 | 4/1991 | European Pat. Off. . |
| 0464480 | 1/1992 | European Pat. Off. ............... 606/232 |
| 520177 | 12/1992 | European Pat. Off. . |
| 0 497 079 | 6/1993 | European Pat. Off. . |
| 0 546 726 | 6/1993 | European Pat. Off. . |
| 0 582 514 | 2/1994 | European Pat. Off. . |
| 0 627 203 | 12/1994 | European Pat. Off. . |
| 2622790 | 5/1989 | France . |
| 2655840 | 6/1991 | France . |
| 2687911 | 9/1993 | France . |
| 2688689 | 9/1993 | France . |
| 2704140A3 | 10/1994 | France . |
| 2529669 | 3/1976 | Germany . |
| 2747312 | 4/1979 | Germany . |
| 2818254 | 10/1979 | Germany . |
| 4127550 | 2/1993 | Germany . |
| 5300917 | 11/1993 | Japan . |
| 1 413 477 | 11/1975 | United Kingdom . |
| 1 485 681 | 9/1977 | United Kingdom . |
| 2227175 | 7/1990 | United Kingdom ..................... 623/11 |
| 2 253 147 | 9/1992 | United Kingdom . |
| WO89/09030 | 10/1989 | WIPO . |
| WO90/08510 | 8/1990 | WIPO . |
| WO92/03980 | 3/1992 | WIPO . |
| WO 96/29029 | 9/1996 | WIPO . |
| WO 98/12991 | 4/1998 | WIPO . |
| WO 98/12992 | 4/1998 | WIPO . |

OTHER PUBLICATIONS

European Patent Abstracts, Week 9118, p. 74, EP 424–734–A.

European Patent Abstracts, Week 9133, p. 77, EP 440–991–A.

European patent Abstracts, Week 9133, EP 441–065–A.

European Patent Abstracts, Week 9134, p. 177, EP 442–629–A.

Kurosaka M. et al., Am. Journal of Sports Med., vol. 15, No. 3, pp. 225–229, "a Biochemical Comparison of Different Surgical Techniques of Graft Fixation in Anterior Cruciate Ligament Reconstruction".

Lambert K.L., Clinical Orthopedics and Related Research, No. 72, Jan./Feb. 1983, pp. 85–89, "Vascularized Patella Tendon Graft with Rigid internal Fixation for Anterior Cruciate Ligament Insufficiency".

Steiner et al., "Anterior Cruciate Ligament Graft Fixation," The American Journal of Sports Medicine, (22) 2:240–247, Mar./Apr. 1994.

FIXATION OF CRUCIATE LIGAMENT GRAFTS

TECHNICAL FIELD

The present invention relates to a method for the reconstruction of a cruciate ligament of a patient. More particularly it relates to such a method in which a graft is used to replace a ruptured anterior or posterior cruciate ligament The present invention also relates to a device for use in such cruciate ligament reconstruction operations.

BACKGROUND ART

As is well known the human knee comprises an articulation of the femur, the tibia and the patella. The femur and the tibia are maintained in a condition of stable articulation by a number of ligaments of which the principal ones are the anterior and posterior cruciate ligaments and the collateral ligaments. The rupture of the anterior cruciate ligament is relatively commonly encountered as a result of sporting injury or the like. This rupture leads to knee instability and can be a debilitating injury. Though less common the rupture of the posterior cruciate ligament can be equally disabling.

There have been a number of procedures designed to reconstruct the anterior cruciate ligament. Initially, attempts were made to replace the anterior cruciate ligament with tendons harvested from elsewhere in the body. These tendons were connected respectively to the femur and the tibia by staples, screws or the like inserted exteriorly into the bone and forming an external attachment to which the tendon could be connected externally of the bone. In some cases, the tendon passed over the top of one of the femoral condyles before attachment to the femur and in other cases a hole was drilled through the femur from outside the bone into the intercondylar notch. These attempts at cruciate ligament reconstruction had mixed success. The tendon tended to break at its point of connection to the bone, or become loose over time, indicating that the tendon bone interface was crucial for effective cruciate ligament reconstruction.

These problems led to the use of bone-tendon-bone grafts generally harvested from mid-third patella tendon with a bone block at each end. Each bone block is inserted into an appropriate hole drilled in the femur or the tibia and secured in place by a screw driven between the wall of the hole and the bone block. While this system has been very successful in many respects a significant number of patients continue to have patella-femoral problems, especially over the mid-third patella tendon donor site.

In an effort to overcome these problems it has been proposed to suture hamstring tendon to a bone block derived from coring the tibial tunnel and to thereby manufacture a bone/tendon/bone graft similar to a mid-third patella tendon graft. The present inventors have found that the bone quality is extremely variable. This results in poor fixation and poor intra-operative pull-out strength in some cases. This procedure was also found to be a very demanding surgical procedure, and therefore difficult to reproduce.

It is also known to provide a method for the reconstruction of the anterior cruciate ligament of a patient which comprises the steps of:

a) forming a tendon graft from tendon, other soft tissue or artificial tendon;

b) forming a hole through the patient's femur from a suitable point in the intercondylar notch therein anteriorly and laterally, the cross-sectional area of at least an end portion of the hole through the femur adjacent the intercondylar notch being sufficient to receive an end of the tendon graft and a suitable screw, peg or other fixation device having a leading end and a trailing end;

c) forming a suitably positioned hole through the patient's tibia opening at one end adjacent the cross-sectional medial tibial spine of the tibia of an area sufficient to receive the other end of the tendon graft;

d) drawing one end of the tendon graft into the enlarged end portion of the hole in the femur and simultaneously or sequentially drawing the other end of the tendon graft into the hole in the tibia;

e) inserting the leading end of a fixation device into the hole in the femur from the intercondylar notch end thereof until the trailing end of the fixation device is at least adjacent that end of the hole, and the tendon graft is pressed directly and firmly against a sidewall of the hole in the femur by the fixation device; and f) after tensioning the tendon graft appropriately, securing the other end of the tendon graft to the tibia.

The foregoing method is a significant improvement over the preceding methods however it still suffers from the theoretical and practical problems of placing a screw or like fastener into a blind hole between the graft and the bone surrounding the hole. The present invention provides the public with an alternative that does not necessarily require the placement of a screw into the hole carrying the graft through either the tibia or the femur.

DISCLOSURE OF INVENTION

In a first aspect the present invention consists in a method for the reconstruction of a cruciate ligament of a patient comprising the steps of:

a) forming a graft from tendon, other soft tissue or artificial tendon;

b) forming a hole through the patient's femur opening at one end at a suitable point in the intercondylar notch in the femur;

c) forming a suitably positioned hole through the patient's tibia opening at one end adjacent the cross-sectional medial tibial spine of the tibia;

d) connecting one end of the graft to the elongate shaft of a connection device, which device comprises an elongate shaft and a cross member pivotally connected intermediate its ends to one end of the elongate shaft;

e) passing the connection device into the hole in the femur from the intercondylar notch end thereof with the cross member lying alongside the elongate member until the cross member extends completely from the other end of the hole in the femur;

f) rotating the cross member so that it lies transversely to the elongate member and pulling the connection device back so that the cross member lies against the surface of the femur;

g) simultaneously or sequentially drawing the other end of the graft at least into the hole in the tibia; and h) after tensioning the graft appropriately, securing the other end of the tendon graft to the tibia.

In a second aspect the present invention relates to a connection device for connecting a cruciate ligament replacement graft to the femur of a patient, the connection device including an elongate member that is pivotally connected at one end to a cross member intermediate its ends, the elongate member being provided, preferably at or adjacent its other end, with means to enable it to be connected to a suitable graft.

The arrangement according to the present invention, at least in preferred embodiments, is that the femoral end of the graft is held in the femoral hole without any spring or elasticity in the connection between the graft and the femoral bone. At this end of the graft, at least, the practical and theoretical problems of screw fixation are avoided.

In preferred embodiments of the invention the elongate member of the connection device has a hook at the one end so that it may be conveniently pivotally connected to the cross member. It preferably has at its other end means to enable the graft to be connected to the elongate member. A suture is preferably connected to each end of the cross member to assist in passing the connection device into, and partially through, the hole in the femur. Tension on one of these sutures and on the graft, in opposite directions, will hold the cross member in its orientation alongside the elongate member. When the cross member projects from the hole this tension is released and the cross member is pivoted into a position in which it lies transversely to the elongate member by pulling on the other of the sutures connected to the cross member. In this position any tension on the graft is resisted by the cross member bearing against the surface of the femur adjacent to the outside end of the hole.

The means to enable the graft to be connected to the elongate member comprise, in one preferred embodiment of the invention, an eye through which the graft may be threaded. The eye is preferably formed by an annular extension of the elongate member. This annular extension preferably has a cross-sectional dimension such that when a graft is draped through the eye and the elongate member positioned in the hole the graft will be firmly engaged on both sides of the eye with the bone surrounding the hole. In this embodiment of the invention the elongate member is preferably of such a length that the eye will be only just completely inside the hole at its condylar notch end. Such an arrangement ensures that there is very little stretch of the graft within the hole. This avoidance of relative motion between the graft and the surrounding bone is believed to assist in the growth of bone into the graft and thereby the establishment of an intimate bond between the bone and the graft.

In the event that the graft comprises a number of graft strands that are connected to the connection means by draping the graft strands through an eye at the other end of the elongate member it is advantageous if the shape of the eye is adapted to mimic the natural connection of cruciate ligament to the femur. The femoral attachment of cruciate ligaments, and particularly the posterior cruciate ligament, to the femur is typically crescent shaped. As the knee is flexed the various strands of the natural ligament will be differentially tensioned. This situation may be imitated by providing that the inside surface of the eye is arcuate with a portion of that surface diametrically opposite the elongate member closer to the elongate member than portions on either side of that portion, i.e. the inside surface of the eye opposite the elongate member bulges radially inwardly.

In a third aspect the present invention relates to connection means for connecting a cruciate ligament graft to a patient's femur, the connection means having a body that has at one end an eye or like formation through which the graft may be threaded, the eye or like formation having a bearing surface against which the graft will, in use, bear, the bearing surface being arcuate along its length and having a portion intermediate its ends that is closer to the body of the connection means than portions on either side of that portion.

In another embodiment of the invention the other end of the elongate member is provided with a hook that can be positioned to extend through a transverse hole through a bone block at an end of the graft. There are circumstances in which the most suitable graft will have a bone block at one or both ends of the graft. The bone block is preferably so sized that it is a tight fit in at least one dimension in the hole as this will assist integration of the bone block with the bone surrounding the hole.

In a preferred embodiment of the invention the tendon graft comprises tendon or tendons derived from the hamstring tendons of the patient or from the Achilles tendons of cadavers. Most preferably, the tendons are the semitendonosus and gracilis tendons of the patient harvested from the same leg as has the deficient cruciate ligament. The invention could be practiced using artificial tendon material or other bodily soft tissue such as ligament. Suitable synthetic plastics materials have been proposed for use in biological applications and could be used in place of natural tendon.

The tendon or tendons forming the tendon graft are preferably doubled over about their mid-point and trimmed to a desired length. The free ends are preferably then bound together, over a length approximately equal to the length of the tendons that will extend through the hole in the tibia, after being threaded through the eye in the connection device. Preferably, the ends of the tendon or tendons will be bound together using a Krakow suture, a roman sandal suture or a modified baseball stitch. A suture may also be connected to the graft at the tibial end. This suture may be used to draw the tendon graft through the tibial hole and to tension the graft prior to insertion of the fixation device in the tibia. This suture may also be used to connect the graft to fixation means on the surface of the tibia.

The tibial hole is preferably formed by drilling a hole having a cross-sectional area just sufficient to receive the other end portion of the tendon graft. As the tendon graft may vary in cross-sectional area along their length it is usual to position the larger end of the tendon or tendons in the tibial hole. In the case of an anterior cruciate ligament replacement a guide hole is preferably drilled from the outside and is guided so that at its exit from the tibia it will be at the coronal level of the median tibial eminence ⅔ of the way across the notch, lateral to medial, so as to remove the anterior cruciate ligament stump. The aim of positioning is so that the final hole causes the graft to arise from the centre of the notch coronally, sufficiently posterior to avoid impingement with the roof of the notch at full extension of the knee.

The graft may be secured in the tibia in any one of a number of different ways. A screw could, for instance, be positioned between the graft and the tibial bone surrounding the hole therein. In an alternative, and more preferred, embodiment of the invention the free end of the graft may be drawn right through the tibial hole and secured, directly or by sutures, to the lateral surface of the tibia by suitable fastening means such as staples, staple plates, or screws. In the latter case both ends of the graft would be anchored into cortical bone which has a number of obvious practical advantages.

As it is preferred to connect the free end of the graft directly, or through a suture, to the cortical bone on the surface of the tibia it would be desirable to be able to bring the graft firmly into contact with the tibial bone surrounding this hole in a manner that substantially prevents movement of the graft within that hole. In order to achieve this it is preferred that, when the graft is made up of a number of strands, to position between the strands an abutment means and to draw this abutment means tightly against the graft strands and to urge them into contact with the tibial bone around or within the hole.

In a fourth aspect the present invention relates to a method for connecting a multi-strand graft to a bone comprising the steps of causing the graft to extend through a hole in the bone, positioning an abutment means between the strands of the graft and drawing the abutment means against the strands of the graft to urge them into contact with the bone surrounding the hole. The abutment means preferably comprises a sphere or similarly shaped object, the abutment means could, however be conical, frusto-conical, pyramidal or any other suitable shape. The abutment means preferably has at least one hole, more preferably at least two holes, extending through it such that when the abutment means is in position in the hole in the tibia the holes in the abutment means will extend transversely to the axis of the hole in the tibia. Sutures are preferably positioned to extend through the hole or holes in the abutment means and through the hole in the bone, these sutures may be used to pull the abutment means tightly into contact with the bone surrounding the hole.

BRIEF DESCRIPTION OF DRAWINGS

The following description of a preferred embodiment of the present invention is provided as an example of the invention and is described with reference to the accompanying drawings, in which.

BEST MODE FOR CARRYING OUT THE INVENTION

Operating Protocol

The following protocol assumes the operator will be securing a graft 10 in replacement of an anterior cruciate ligament on the femoral side 11 from within the joint and on the tibial side 12 externally. The graft 10 consisting of semitendonosus and gracilis tendons 13 and 14 respectively is also assumed.

Preparation

Routine arthroscopy is performed prior to commencement of reconstruction of the anterior cruciate ligament. Portal placement is critical and can be described thus: the anterolateral portal (not shown) is towards the top of the lateral triangle soft spot. It is made with a transverse stab incision, aimed at the intercondylar notch 15. The anteromedial portal 18 is lower than usual, being 1 cm above the joint line and at the fat pad reflection, with the blade aimed slightly up and towards the intercondylar notch.

At this time, using the arthroscope in the anterolateral portal, any meniscal repair or excision is carried out as well as any debridement required for adequate visualisation of the joint in general and the notch in particular. Often this requires partial excision of the fat pad and particularly careful clearing of the notch surface of the lateral condyle of the femur. The scar tissue associated with the ruptured cruciate, the stump of the anterior cruciate ligament and the plica interaricularis should also be debrided. A curette is used to clear the lateral wall of the notch and a suction shaver may be used to remove the resultant debris.

Figure 1:
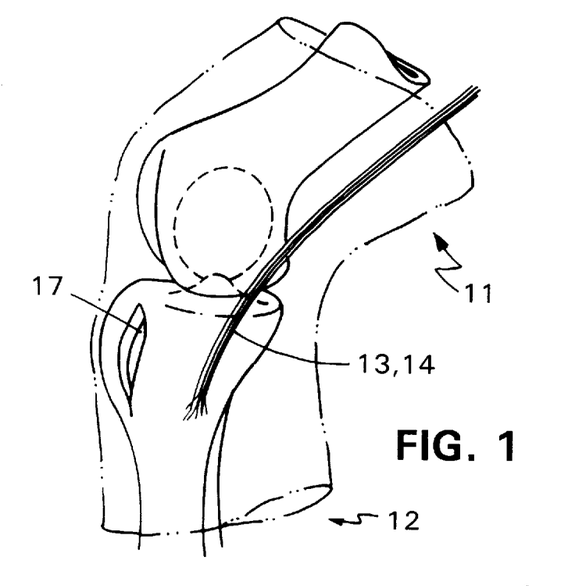
FIG. 1 is a schematic perspective view of a patient's knee showing the position of the semitendonosus and gracilis tendons and the incision through which these tendons are harvested to form a graft.

The semitendonosus and gracilis tendons 13 and 14 are then harvested as graft material. This should be done in whatever fashion the operator is comfortable with, however, a single incision 17 approximately 30 millimeters is all that is required. The incision is medial to the tibial tubercle at the level of the pes anserine insertion. The harvesting of the semitendonosus and gracilis tendons 13 and 14 should result in at least 22 cm of the tendons. Separation of the tendon should occur at the musculo-tendinous junction. Care should be taken in harvesting the tendons to ensure the accessory distal insertions of the semitendonosus in particular are divided and do not divert the harvesting tool into the body of the tendon.

Figure 2A:
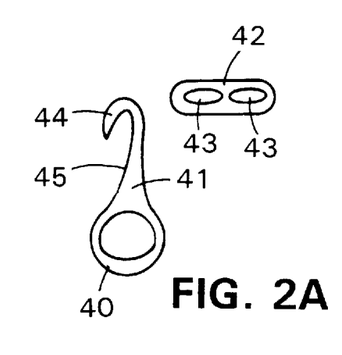
FIG. 2A is a perspective view of the component parts of a connecting device according to the present invention.
Figure 2B:
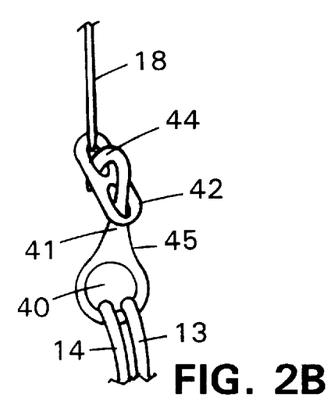
FIG. 2B is a perspective view of the component parts of the connecting device of FIG. 2A assembled together and connected to a suture and to a graft.
Figure 2C:
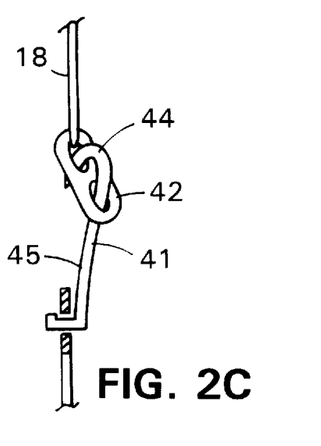
FIG. 2C is a partially sectional view of a connecting device according to a second embodiment of the present invention connected to a graft having a terminal bone block.

After the tendons 13 and 14 are cleared of adherent muscle fibers their length should be measured and the mid-point determined, ideally this is 11 cm from the distal insertion of the tendons. The broad surface of the semitendonosus 13 is wrapped around the tendon mass using this tendon to give a smooth exterior surface to the graft 10. The two tendons 13 and 14 are then doubled over an draped through the eye 40 at one end of a connecting device 41 (see FIG. 2B). The connecting device 41 has at its other end a toggle 42 which has two holes 43 in it. A hook-like end 44 on the connecting device 41 can extend through the holes 43 to pivotally connect the toggle 42 to the connecting device 41. The four strand hamstring tendon complex 10 may be sutured at its other end with a modified roman sandal stitch 21 to hold the tendons 13 and 14 together.

The diameter of the tendon graft 10 is now measured at both the proximal and distal ends, using a tube gauge. These diameters are noted for appropriate drill sizing. Any free tissue in the graft 10 which may bunch up and obstruct the passing of the graft 10 through the tibial and femoral drill holes should now be noted and excised.

Figure 3:
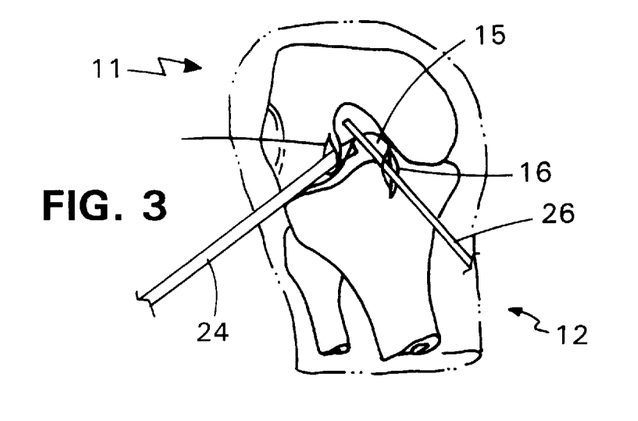
FIG. 3 is schematic perspective view of the patient's knee showing the positioning of an arthroscope and the drilling of a guide hole for the formation of a femoral hole to receive one end of the tendon graft.

Having taken the graft, the arthroscope 24 is then inserted into a central portal through a stab incision 25 over the patella tendon, just below the inferior pole of the patella (not shown), thereby allowing better visualisation of the back of the notch 15. Often it is found that further clearing of the lateral wall of the notch 15 is required. This should be performed until the capsular attachment is clearly visualised and palpated with a probe.

Femoral Drilling

A point 30° from the top of the notch (11 o'clock in a right knee; 1 o'clock in a left knee) and 5 mms from the back of the notch 15 on the lateral wall is then identified and indented with a burr. Care must be taken to avoid identifying the ridge of the anterior edge of the original ACL attachment as the back of the notch (resident's ridge). This error will lead to the femoral tunnel being too anterior, compromising graft function. A 4.5 mm drill 26 is then passed into the joint through the medial portal 16 and the tip placed in the burr hole while the knee is held at 90° (the use of standard tissue protecting sleeves is recommended). The drill is the spun a few turns to bed it into this depression.

Holding the drill tip in the shallow hole thus created the knee is pushed into as much flexion as it will achieve. Directing the drill approximately 20° anteriorly and 30° laterally with respect to the femur, a guide hole is then made, with drilling ceasing as soon as the outer cortex is felt to have been pierced. Withdraw the drill 26 and inspect the hole 29 to confirm position by passing the arthroscope deep into the notch.

Figure 4:
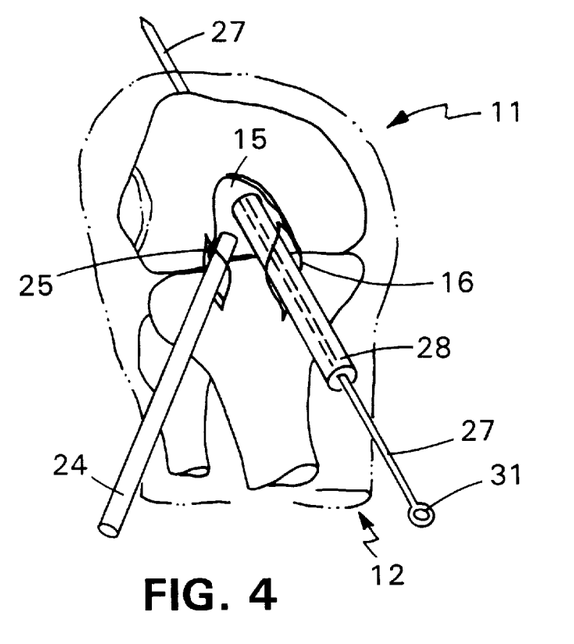
FIG. 4 is a schematic perspective view showing a cannulated drill on a beath pin being used to form the femoral hole.

With the knee at 90° flexion, a beath pin 27 is then passed through the medial portal and up to the entrance of the guide drill hole under direct vision. Care should be taken not to pass the pin 27 through the posterior cruciate ligament The knee is flexed maximally and the pin 27 is passed up the guide hole and out through the skin. This pin 27 serves as the guide for a cannulated drill 28. With the knee held fully flexed a cannulated drill 28 of a diameter matching the tendon graft, is then passed along the pin 27 and, under direct vision, the femoral hole 29 made.

The drill 28 is then removed and a nylon loop (not shown) threaded into the eye 31 of the beath pin 27. With the loop end held, the pin 27 is drawn out of the femur and the free ends of the nylon and drawn through the femoral hole 29 and out of the thigh. Smoothing of the edge of the femoral hole and debridement of any loose tissue is now carried out.

Figure 5:
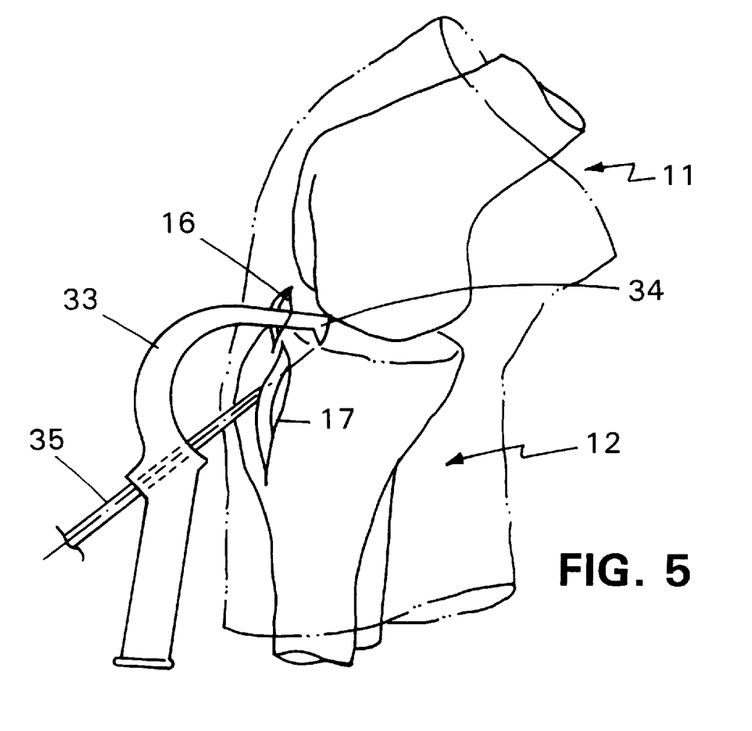
FIG. 5 is a schematic perspective view showing the drilling of a guide hole for a tibial hole to receive the other end of the tendon graft.

The tibial hole is then made with the use of a guide 33. The tip 34 of the guide 33 is passed through the anteromedial portal 16 and placed on a line from the anterior horn of the lateral meniscus to the medial tibial spine and medially, one quarter of the way across the intercondylar notch, that is just medial to the medial tibial spine. The drill guide 33 then passes through the distal skin incision 17 used for the harvesting of the hamstring tendon graft 10 and measures 40–45 mm distal from the cruciate ligament tibial attachment. The 4.5 mm drill 35 is used to establish the line until the cortex of the tibial plateau is reached, whereupon the guide is removed and the drilling completed under direct vision. The final position may be fine tuned by hand, so that the final drill position will abut the medial eminence and remove the anterior cruciate ligament stump. Having achieved satisfactory placement of the 4.5 mm drill 35, a 2.0 mm guide wire (not shown) is passed into the hole. The guide wire should intersect the PCL near its femoral insertion to indicate correct drill hole placement and alignment. A cannulated drill (not shown but similar to drill 28) of a diameter equal to that of the tendon graft's distal end can now be introduced over the guide wire. When tibial hole enlargement is completed, the soft tissue at the entry to the joint can be cleared with a shaver.

Figure 6:
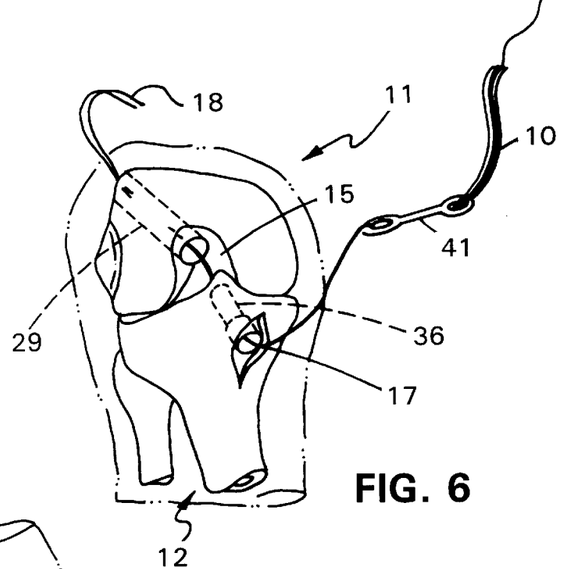
FIG. 6 is schematic perspective view of drawing the tendon graft through the tibial hole into the femoral hole.
Figure 7:
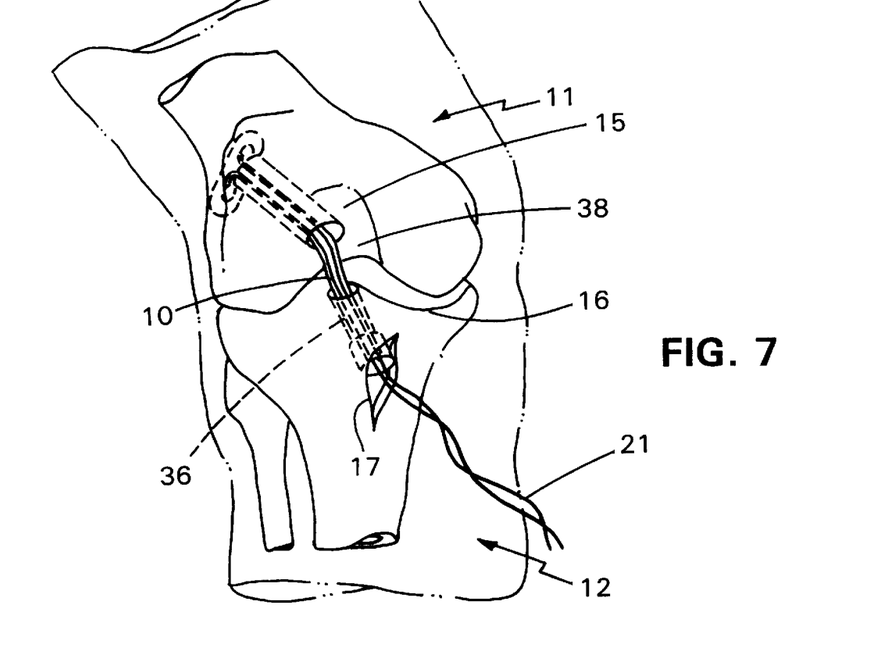
FIG. 7 is a schematic perspective view showing the placement of a connecting device to secure the one end of the tendon graft in the femoral hole.
Figure 11:
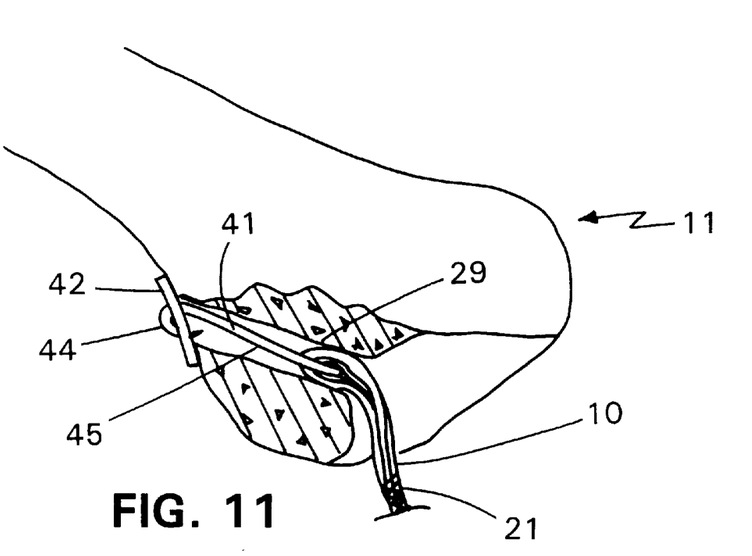
FIG. 11 is a vertical sectional view of a connecting device positioned in the femoral hole and securing the one end of the tendon graft to the femur.

The suture 18 connected to one end of the toggle 42 is then used to draw the connecting device 41 through the tibial hole 36 into the femoral hole 29 until the toggle 42 is just drawn past the posterior end of the hole 29. The suture 28 is connected to the toggle 42 so that the toggle is caused to lie alongside the shaft 45 of the connecting device 41, which lies between the eye 40 and the hook-like member 44. Once the toggle 42 is free of the hole 29 the tension in the suture 18 is released and suture 18a connected to the other end of the toggle 42 is tensioned and the pull back in order to pivot toggle 42 into a position in which it lies against the outside face of the femur adjacent the femoral hole 29. The tendon complex 10 is thus connected to the femur.

Figure 8:
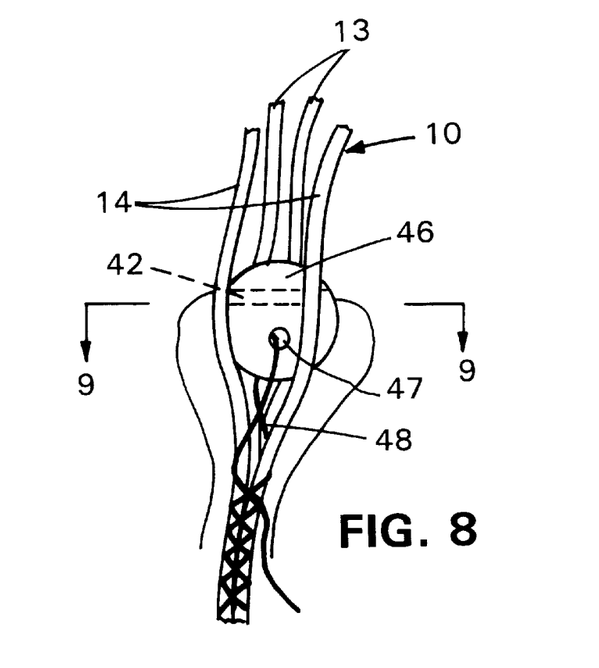
FIG. 8 is a detailed perspective view of a bead used to hold graft strands in contact with the tibia.
Figure 9:
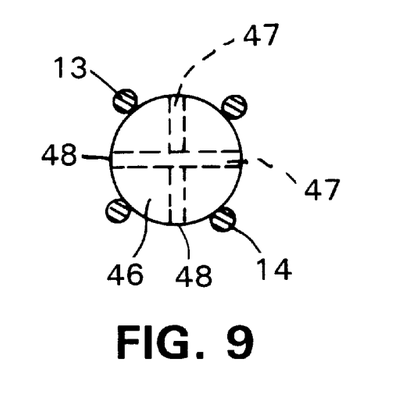
FIG. 9 is a section along IX—IX of FIG. 8

A bead 46, having orthogonally arranged holes 47 formed through it, is previously positioned between the four strands of tendon 13 and 14. Sutures 48 extend through the holes 47 in the bead and one end of one suture is positioned to extend between each of the tendon strands 13 and 14.

Figure 12:
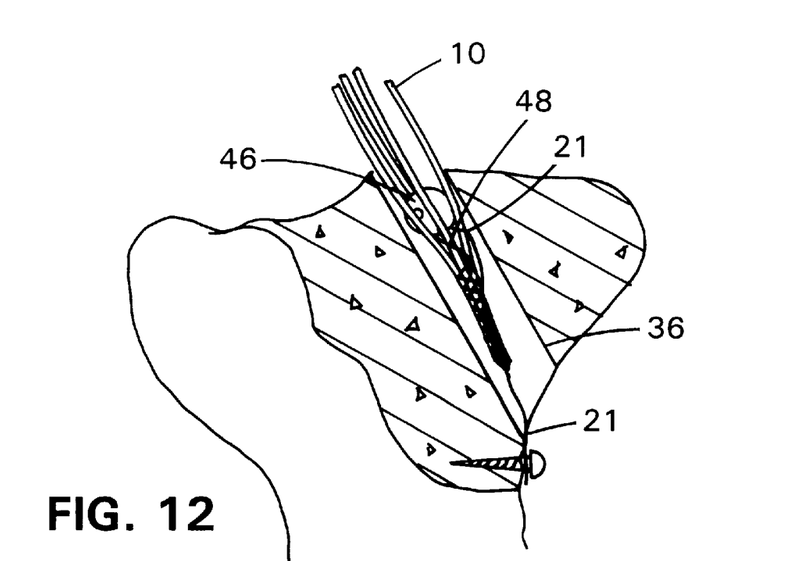
FIG. 12 is a vertical sectional view of the other end of the graft secured to the tibia.

The end of the suture 21 and the ends of the sutures 48 are then pulled into tension in the tibial thereby drawing the tendon complex 10 hole 36 and drawing the bead 46 firmly into contact with the tendon strands 13 and 14. The tension transferred by the sutures 48 to the bead 46 forces the tendon strands which typically are thicker at the tibial end into contact with the tibial bone surrounding the tibial hole 36. The contact between the tendon strands 13 and 14 and the tibial bone helps integration of bone growth into the tendon in two ways. Firstly it prevents longitudinal movement of the tail of the tendon complex 10 within the tibial hole 36 (called 'pistoning') which prevents the growth of solid bone and secondly the pressure of the tendon on the bone itself promotes bone growth.

Figure 10:
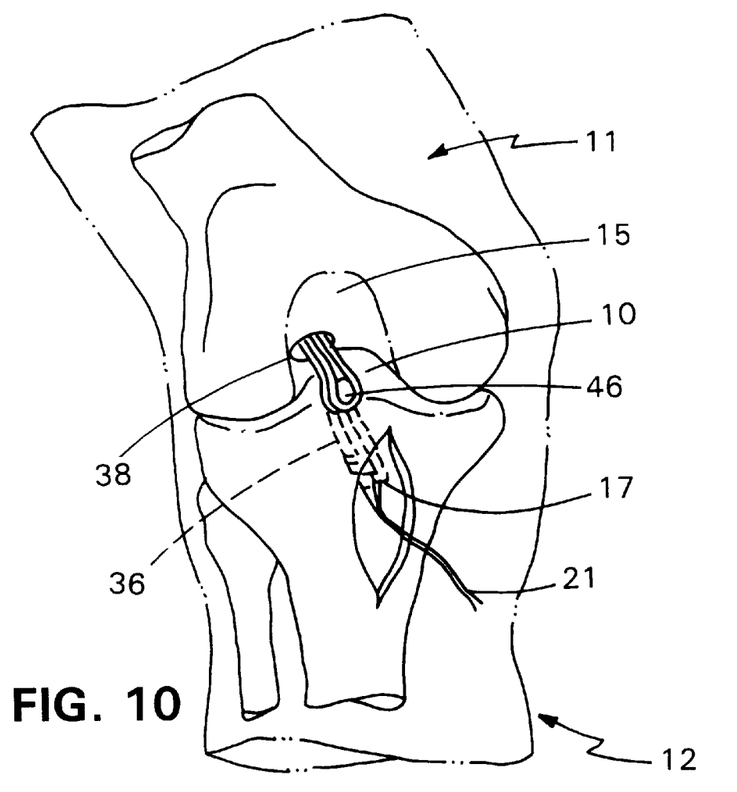
FIG. 10 is a schematic perspective view showing the placement of a screw to secure the other end of the tendon graft to the tibia.

Having fixed the femoral end of the tendon graft 10, the knee is placed at 90° flexion and the tibial end 23 drawn down firmly, thereby applying tension to the graft 10. Isometricity may be tested at this time as the knee is extended and flexed. Having achieved the desired tension and positioning of the graft 10. While maintaining distal tension on the graft 10, and holding the knee at 30–45° of flexion, a screw 41 is inserted into the tibia outside the tibial hole 36 and the suture 21 connected to it in a known manner.

The motion of the knee, Lachman test, anterior draw and pivot shift test are finally checked. The knee is copiously irrigated to remove debris. A drain is passed into the joint using the arthroscopic procedure and directly laterally. Routine closure and post-operative care is followed.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A connection device for connecting a cruciate ligament replacement graft to a femur of a patient, the connection device including an elongate member that is pivotally connected at one end to a cross member intermediate its ends, the elongate member being provided, at or adjacent its other end, with means to enable it to be connected to a suitable graft.

2. The connection device of claim 1 wherein the elongate member of the connection device has a hook at the one end so that it may be conveniently pivotally connected to the cross member.

3. The connection device of claim 1 wherein the elongate member has at an end distal the one end means to enable the graft to be connected to the elongate member.

4. The connection device of claim 3 wherein a suture is connected to each end of the cross member to assist in passing the connection device into, and partially through, a hole in the femur.

5. The connection device of claim 4 wherein the means to enable the graft to be connected to the elongate member comprise an eye through which the graft may be threaded.

6. The connection device of clam 5 wherein the eye is formed by an annular extension of the elongate member.

7. The connection device of claim 6 wherein the annular extension has a cross-sectional dimension such that when a graft is draped through the eye and the elongate member positioned in the hole the graft will be firmly engaged on both sides of the eye with the bone surrounding the hole.

8. The connection device of claim 6 wherein the elongate member is of such a length that the eye will be only just completely inside the hole in the femur at its condylar notch end.

9. The connection device of claim 1 wherein in the event that the graft comprises a number of graft strands that are connected to the connection means by draping the graft strands through an eye at the other end of the elongate member, the connection between the graft and the eye approximates the natural connections of cruciate ligament to the femur.

10. The connection device of claim 9 wherein the inside surface of the eye is arcuate with a portion of that surface diametrically opposite the elongate member closer to the elongate member than portions on either side of that portion.

11. A connection means for connecting a cruciate ligament graft to a patient's femur, the connection means having a body that has at one end an eye or like formation through which the graft may be threaded, the eye or like formation having a bearing surface against which the graft will, in use, bear, the bearing surface being arcuate along its length and having a portion intermediate its ends that is closer to the body of the connection means than portions on either side of that portion.

12. The connection device of claim 11 wherein the end of the body distal the one end is provided with a hook that can be positioned to extend through a transverse hole through a bone block at an end of the graft.

13. The connection device of claim 11 wherein the graft includes a bone block at one or both ends of the graft.

14. The connection device of claim 13 wherein the bone block is so sized that it is a tight fit in at least one dimension in a hole in the femur or a hole in a tibia so as to assist integration of the bone block with the bone surrounding the hole.

15. The connection device of claim 11 wherein the tendon graft comprises tendon or tendons derived from the hamstring tendons of the patient or from the Achilles tendons of cadavers.

16. The connection device of claim 15 wherein the tendons are the semitendonosus and gracilis tendons of the patient harvested from the same leg as the deficient cruciate ligament.

17. A method for the reconstruction of a cruciate ligament of a patient comprising the steps of:
 a) forming a graft from tendon, other soft tissue or artificial tendon;
 b) forming a hole through the patient's femur opening at one end at a suitable point in the intercondylar notch in the femur;
 c) forming a suitably positioned hole through the patient's tibia opening at one end adjacent the cross-sectional medial tibial spine of the tibia;
 d) connecting one end of the graft to an elongate shaft of a connection device, which device comprises the elongate shaft and a cross member pivotally connected intermediate its ends to one end of the elongate shaft;
 e) passing the connection device into the hole in the femur from the intercondylar notch end thereof with the cross member lying alongside the elongate member until the cross member extends completely through the hole in the femur;
 f) rotating the cross member so that it lies transversely to the elongate member and pulling the connection device back so that the cross member lies against the surface of the femur;
 g) simultaneously or sequentially drawing the other end of the graft at least into the hole in the tibia; and
 h) after tensioning the graft appropriately, securing the other end of the tendon graft to the tibia.

18. The method of claim 17 wherein the tendon or tendons forming the tendon graft are doubled over about their mid-point and trimmed to a desired length.

19. The method of claim 18 wherein the resulting free ends are then bound together, over a length approximately equal to the length of the tendons that extend through the hole in the tibia, after being threaded through the eye in the connection device.

20. The method of claim 19 wherein the ends of the tendon or tendons are bound together using a Krakow suture, a roman sandal suture or a modified baseball stitch.

21. The method of claim 20 wherein a suture is connected to the graft at the tibial end, the suture being used to draw the tendon graft through the tibial hole and to tension the graft prior to insertion of the fixation device in the tibia.

22. The method of claim 21 wherein the suture is also used to connect the graft to fixation means on the surface of the tibia.

23. The method of claim 17 wherein the tibial hole is formed by drilling a hole having a cross-sectional area just sufficient to receive the other end portion of the tendon graft.

24. The method of claim 17 wherein in the case of an anterior cruciate ligament replacement, a guide hole is drilled from the outside and is guided so that at its exit from the tibia it will be at the coronal level of the median tibial eminence ⅔ of the way across the notch, lateral to medial, so as to remove the anterior cruciate ligament stump.

25. The method of claim 17 wherein the free end of the graft is drawn right through the tibial hole and secured, directly or by sutures, to a lateral surface of the tibia by suitable fastening means such as staples, staple plates, or screws.

26. The method of claim 25 wherein the graft is brought firmly into contact with the tibial bone surrounding this hole in a manner that substantially prevents movement of the graft within that hole.

27. A method for connecting a multi-strand graft to a bone comprising the steps of extending the graft through a hole in the bone, positioning an abutment means between the strands of the graft and drawing the abutment means against the strands of the graft to urge them into contact with the bone surrounding the hole.

28. The connection device of claim 1, wherein the elongate member is inelastically connected to the cross member.

29. The connection device of claim 9, wherein the eye is crescent shaped.

* * * * *